United States Patent [19]
Patel

[11] 4,447,228
[45] May 8, 1984

[54] CATHETER

[75] Inventor: Bhupendra C. Patel, Elgin, Ill.

[73] Assignee: The Kendall Company, Walpole, Mass.

[21] Appl. No.: 411,254

[22] Filed: Aug. 25, 1982

Related U.S. Application Data

[60] Division of Ser. No. 146,421, May 5, 1980, Pat. No. 4,361,152, which is a continuation of Ser. No. 930,386, Aug. 2, 1978, abandoned, which is a continuation of Ser. No. 767,425, Feb. 10, 1977, abandoned, which is a continuation of Ser. No. 581,251, May 27, 1975, abandoned.

[51] Int. Cl.³ .................................................. A61M 25/00
[52] U.S. Cl. .................................................. 604/103
[58] Field of Search ............... 128/348.1; 604/96–103, 604/905

[56] References Cited

U.S. PATENT DOCUMENTS

| Re. 27910 | 2/1974 | Birtwell | 128/349 B |
|---|---|---|---|
| 3,292,627 | 12/1966 | Harautuneian | 128/349 B |
| 3,460,540 | 8/1969 | Gagne | 128/349 R |
| 3,544,668 | 12/1970 | Dereniuk | 128/349 B X |
| 3,547,126 | 12/1970 | Birtwell | 128/349 |
| 3,734,100 | 5/1973 | Walker et al. | 128/351 |
| 3,736,939 | 6/1973 | Taylor | 128/349 B |
| 3,742,959 | 7/1973 | Patel | 128/349 B |
| 3,799,172 | 3/1974 | Szpur | 128/349 R |
| 3,805,794 | 4/1974 | Schlesinger | 128/349 R |
| 3,812,860 | 5/1974 | Gilbert et al. | 128/349 B |
| 3,832,253 | 8/1974 | DiPalma et al. | 128/349 B X |
| 3,884,242 | 5/1975 | Bazell et al. | 128/349 B X |
| 3,896,815 | 7/1975 | Fettel et al. | 128/349 B |
| 3,926,705 | 12/1975 | Todd | 128/349 B X |
| 3,986,508 | 10/1976 | Barrington | 128/214.2 |

Primary Examiner—Michael H. Thaler

[57] ABSTRACT

A catheter comprising, an extruded tube having a drainage lumen and inflation lumen, with the inflation lumen communicating with the outside of the tube through opening means. The catheter has a tip secured to a distal end of the tube, and an annular sleeve extending from the tip and having a proximal end secured to the outside of the tube.

1 Claim, 6 Drawing Figures

U.S. Patent            May 8, 1984            4,447,228
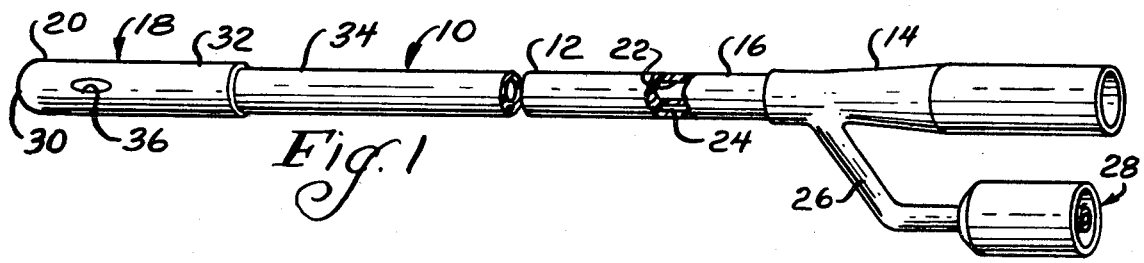
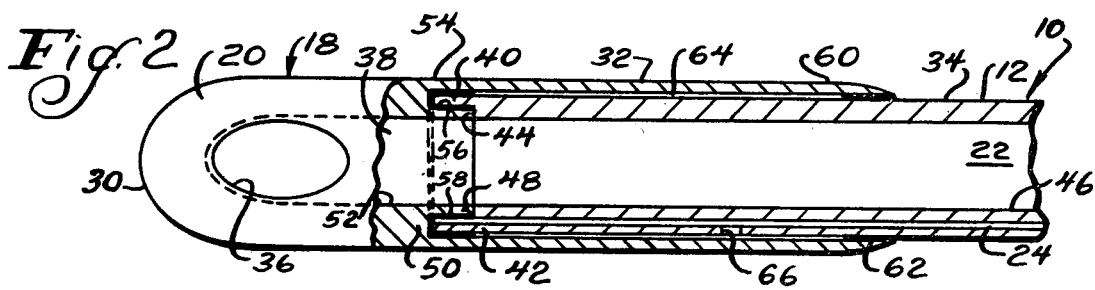
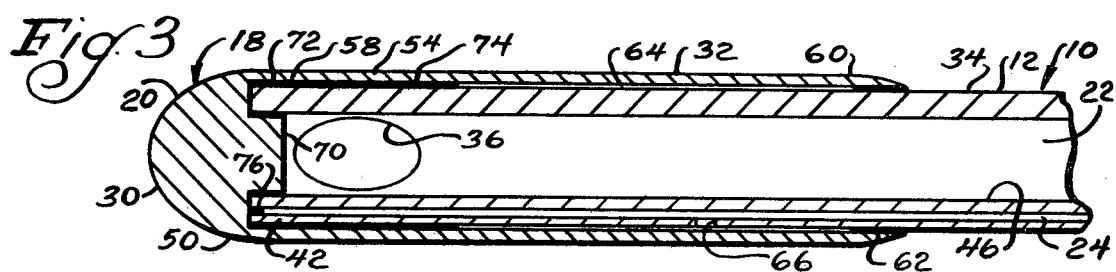
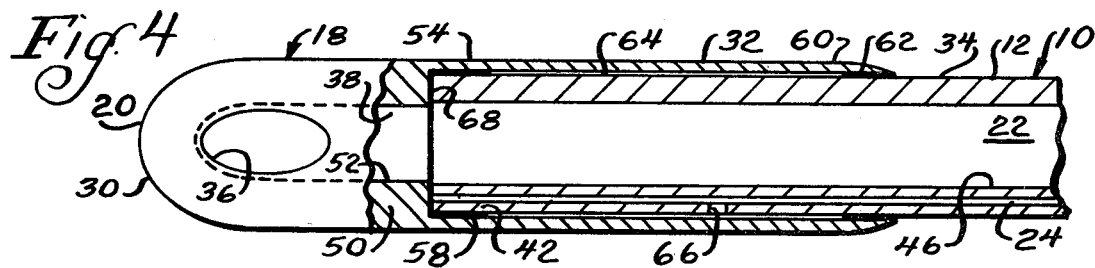
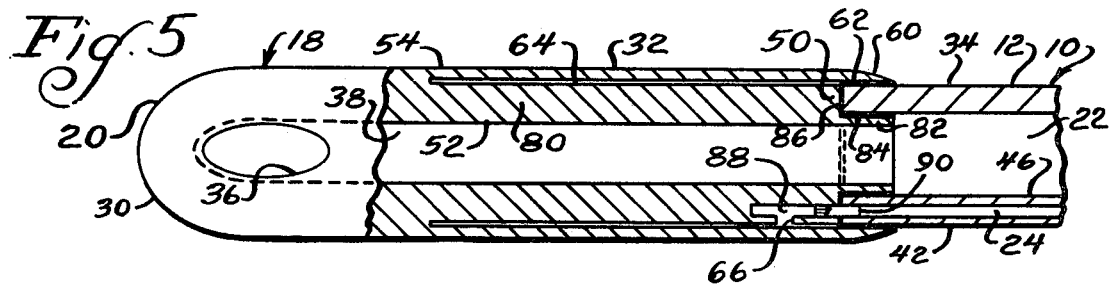
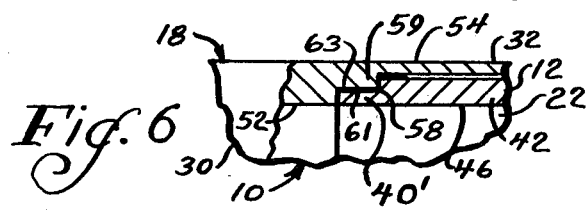

CATHETER

This application is a division of application Ser. No. 146,421, filed May 5, 1980 and now U.S. Pat. No. 4,361,152, issued Nov. 30, 1982, which is a continuation of application Ser. No. 930,386 filed Aug. 2, 1978 and now abandoned, which is a continuation of application Ser. No. 767,425 filed Feb. 10, 1977 and now abandoned, which is a continuation of application Ser. No. 581,251 filed May 27, 1975 and now abandoned.

BACKGROUND OF THE INVENTION

The present invention relates to catheters.

Conventional Foley catheters have often been made from latex rubber through dipping techniques. Although such catheters are in widespread use, on occasion their inflation lumens become obstructed during use, thus preventing deflation of their retention balloons which are inflated in the patient's bladder. More recently, different materials have been used to make urinary retention catheters. Some of these materials may be extruded to form the catheter shaft and inflation lumen, thus substantially eliminating nondeflation problems associated with the inflation lumen. Additionally, some of the materials are believed less toxic to the patient than latex rubber.

Although certain difficulties have been solved through use of different materials, the retention balloon must be formed in a different manner. The retention balloon and catheter tip may be made in a single assembly, and the assembly may be secured to the distal end of the catheter shaft. However, the bond between the assembly and shaft should be sufficiently strong to prevent severance during use, and the tip should be sufficiently rigid to permit placement in the patient without undue flexation of the tip.

SUMMARY OF THE INVENTION

A principal feature of the present invention is the provision of a catheter of simplified construction and improved strength.

The catheter of the present invention comprises, an extruded tube having a drainage lumen and inflation lumen extending to a distal end of the tube. The inflation lumen communicates with the outside of the tube through opening means. The catheter has a tip assembly comprising a tip secured to the distal end of the tube, and an annular sleeve extending from the tip and having a proximal end secured to the outside of the tube.

A feature of the present invention is that the tip may have an annular groove adjacent its proximal end to receive a distal end portion of the tube.

Another feature of the invention is that the distal portion of the shaft is bonded to the tip in the groove.

Yet another feature of the invention is that a distal portion of the sleeve is bonded to the distal portion of the tube.

Thus, a feature of the invention is that a superior bond is obtained between the tube and tip assembly.

A feature of the present invention is that the tip has sufficient rigidity to permit placement of the catheter in a patient without undue flexation of the tip.

Another feature of the invention is that in one embodiment the tip is secured to the tube adjacent the proximal end of the sleeve Further features will become more fully apparent in the following description of the embodiments of this invention and from the appended claims.

DESCRIPTION OF THE DRAWINGS

In the drawings:

FIG. 1 is a fragmentary elevational view of a catheter of the present invention;

FIG. 2 is a fragmentary sectional view, partly broken away, of a distal end portion of the catheter of FIG. 1;

FIG. 3 is a fragmentary sectional view of another embodiment of the catheter of the present invention;

FIG. 4 is a fragmentary sectional view, partly broken away, of another embodiment of the catheter of the present invention;

FIG. 5 is a fragmentary sectional view, partly broken away, of another embodiment of the catheter of the present invention; and FIG. 6 is a fragmentary sectional view of another embodiment of the catheter of the present invention.

DESCRIPTION OF THE PREFERRED EMBODIMENTS

Referring now to FIG. 1, there is shown a urinary retention catheter generally designated 10 having a shaft 12, a connector 14 secured or bonded to a proximal end 16 of the shaft 12, and a tip assembly 18 defining a distal end 20 of the catheter 10. The catheter 10 has a drainage lumen 22 extending through the shaft 12 and connector 14, and an inflation lumen 24 extending through a wall of the shaft 12 and a sidearm 26 of the connector 14 where it communicates with valve means 28. The tip assembly 18 has a rounded tip 30 at the distal end of the catheter, and a flexible annular balloon or sleeve 32 secured to an outer surface 34 of the shaft 12. In use, a syringe (not shown) is attached to the valve means 28, and fluid is injected through the inflation lumen 24 to inflate the balloon 32 in the patient's bladder after placement of the catheter. Similarly, the syringe is used to withdraw the fluid from the balloon 32 through the lumen 24 to deflate the balloon, preparatory to removal of the catheter from the patient.

As shown in FIGS. 1 and 2, the tip 30 has a pair of drainage eyes which extend through opposite sides of the tip, and which communicate with the drainage lumen 22 through a channel 38 in the tip 30. After placement of the catheter, urine drains through the eyes 36 and drainage lumen 22 of the catheter.

The shaft 12 preferably comprises an extruded tube, and may be made of any suitable material, such as urethane, polyvinylchloride, or silicone. The tip assembly 18 may be made of the same materials, or from latex rubber, may be molded, and may have a modulus of elasticity less than the modulus of elasticity of the shaft or tube 12. The tip assembly 18 may be secured to the tube 12 by suitable means, such as by radio-frequency sealing for certain materials, and by suitable adhesives or solvents, including plastisol, toluene, and silicone adhesives.

As shown in FIG. 2, the tube 12 has an annular tongue 40 at its distal end 42 and adjacent its outer surface 34, with the tongue 40 defining an annular recess 44 adjacent an inner surface 46 of the tube 12. The tip 30 has an annular tongue 48 at its proximal end 50 and adjacent its inner surface 52.

As shown, the sleeve 32 extends from the proximal end 50 of the tip 30 and overlies the outer surface 34 of the tube 12, with the distal end 54 of the sleeve 32 defining an annular groove 56 with the tip tongue 48. The tip tongue 48 is received in the recess 44, and the tube tongue 40 is received in the groove 56 with the tongues 48 and 40 in mating engagement, and with the tongue 48 defining a relatively continuous inner surface of the catheter relative the tube 12. The tongues 48 and 40 are secured together by suitable bonding means 58, as described above, with the bonding means 58 extending throughout the recess 44 and groove 56 and also securing the distal end 54 of the sleeve 32 to the outer surface 34 of the tube 12 at its distal end 42.

The proximal end 60 of the sleeve 32 is secured to the outer surface 34 of the tube 12 circumferentially around the tube by suitable bonding means 62. Thus, the sleeve 32 and tube 12 define an inflation cavity 64 intermediate the bonding means 58 and 62, with the cavity 64 communicating with the inflation lumen 24 through suitable opening means 66 in the tube wall intermediate the proximal and distal ends of the sleeve. The inflation fluid is pumped through the lumen 24 and opening means 66 into the cavity 64 to inflate the sleeve 32.

Thus, in accordance with the present invention, the tip assembly 18 is secured to the tube 12 with the interengaging tongues 40 and 48 providing an improved bond to prevent severance of the tip 30 from the tube 12. The bond between the distal end 54 of the sleeve 32 and the distal end 42 of the tube 12 also enhances the attachment strength between the tip assembly and tube. The tip assembly may be molded, the bonding material may be placed on the tube and tip assembly to form the bonding means 58 and 62, the tip assembly may be placed on the tube, and the tube and tip assembly may be radially compressed to facilitate formation of the bond.

Another embodiment of the catheter, which is similar to the catheter of FIG. 2, is illustrated in FIG. 6, in which like reference numerals designate like parts. In this embodiment, the tip 30 has an annular ledge 59 defining an annular recess 61 adjacent the inner surface 52 of the tip. The tube 12 has an annular tongue 40' at its distal end 42 and adjacent its inner surface 46, with the tongue 40' defining an annular recess 63, which may be formed by grinding, adjacent the outer surface of the tube 12. As shown, the tube tongue 40' is received in the recess 61 and the ledge 59 is received in the recess 63. The tongue 40' and ledge 59 are secured together, and the distal end 54 of the sleeve 32 may be secured to the outer surface of the tube 12 adjacent its distal end, by the bonding means 58.

Another embodiment of the catheter of the present invention is illustrated in FIG. 4, in which like reference numerals designate like parts. In this embodiment, the proximal end 50 of the tip 30 has an annular shoulder 68 which abuts against the annular distal end 42 of the tube 12. Thus, the bonding means 58 secures the shoulder 68 to the distal end of the tube 12, and the distal end 54 of the sleeve 32 to the distal end of the tube at the outer surface of the tube. As shown, the tip shoulder 68 has a greater thickness than the tube to assure that the tube abuts against the shoulder during bonding and to add rigidity to the tip due to the increased amount of material surrounding the channel 38.

Another embodiment is illustrated in FIG. 3, in which like reference numerals designate like parts. In this embodiment, the tip 30 has a cylindrical plug 70 extending from the proximal end 50 of the tip and defining an annular groove 72 with the distal end 54 of the sleeve 32. As shown, the plug 70 is snugly received in the distal end of the drainage lumen 22, and the distal end 42 of the tube 12 is received in the groove 72, with the bonding means 58 securing the plug 70 and the distal end of the tube 12 together.

The bonding means 58 also secures the distal end 54 of the sleeve to the outer surface 34 of the tube 12 at its distal end throughout a zone 74 peripherally around the tube. The drainage eyes 36 are formed through the distal ends of the sleeve and tube in the zone 74, such that aligned openings are defined in the sleeve and tube. The distal end of the tube adds rigidity to the tip assembly 18 beneath the distal end of the sleeve. If desired, the distal end of the inflation lumen 24 may be plugged by suitable means 76, such as a drop of adhesive or solvent.

Another embodiment of the invention is illustrated in FIG. 5, in which like reference numerals designate like parts. In this embodiment, the tip 30 has an elongated shaft 80, and a substantial portion of the sleeve 32 overlies the shaft 80 with the cavity 64 being located intermediate the sleeve 32 and shaft 80. The tip 30 has an annular tongue 82 at its proximal end and adjacent its inner surface 52, with the proximal end 60 of the sleeve 32 and the tongue 82 defining an annular groove 84. As shown, the tongue 82 is received in the distal end of the drainage lumen 22, and the distal end 42 of the tube 12 is received in the groove 84. The bonding means 62 secures the distal end 42 of the tube to the tongue 82, a shoulder 86 of the tip, and the proximal end 60 of the sleeve 32.

As shown, the tip 30 has a passageway 88 adjacent its distal end 50 communicating between the inflation lumen 24 and the opening means 66 leading to the cavity 64 beneath the sleeve 32. A tube section 90 may have one end received in the inflation lumen 24 and its other end received in the passageway 88. The tube section 90 assures that communication is established between the inflation lumen and passageway during assembly of the catheter.

The foregoing detailed description is given for clearness of understanding only, and no unnecessary limitations should be understood therefrom, as modifications will be obvious to those skilled in the art.

I claim:
1. A retention catheter comprising:
an elongated shaft comprising an extruded tube having an outer surface, a distal end, a drainage lumen extending to the distal end of the tube, an inflation lumen extending through the wall of the tube to the distal end of the tube, an opening extending through the wall of the tube communicating between the inflation lumen and the outer surface of the tube, said opening being spaced from the distal end of the tube, and an annular tongue adjacent the outer surface of the tube and at the distal end of the tube, said tongue defining an inwardly-facing annular recess adjacent the drainage lumen at the distal end of the tube;
a tip secured to the tube adjacent its distal end, said tip having an outer surface, a drainage eye communicating with the drainage lumen of said tube, an axially-extending annular recess at the proximal end of said tip, and an axially-extending annular tongue adjacent the inner surface of said tip and at the proximal end of the tip, said tongue of said tip defining the inner surface of said axially-facing annular recess; and an expansible annular sleeve of one-piece construction with said tip, said sleeve extending from the proximal end of the tip at its outer surface to proximal the opening between the inflation lumen and the outer surface of the tube, the distal end of said sleeve circumferentially surrounding the said tongue of said tip and defining the outer surface of said axially-facing annular recess, said tube tongue being received within said axially-facing annular recess of said tip, said tip tongue being received within said annular recess of said tube, and said sleeve distal end being arranged to enshroud said tube tongue, the distal end of said sleeve including an interior surface which is secured to the outer surface of the tube tongue, the proximal end of the sleeve being secured to the outer surface of the tube circumferentially around the shaft, and said tube distal end being secured to an axially-facing surface at the distal end of said tip recess and remote from said sleeve proximal end thus to provide a catheter tip structure less likely to be separated from said tube during use, and said opening communicating between the inflation lumen and the outer surface of the tube being located intermediate said sleeve distal and proximal ends at a point remote from said tube distal end, whereby the patency of said opening will not be compromised during the assembly of said tip with said tube.

* * * * *